(12) United States Patent
Welchel et al.

(10) Patent No.: US 7,488,068 B2
(45) Date of Patent: Feb. 10, 2009

(54) EYEWEAR WITH MASK ATTACHMENT FEATURES

(75) Inventors: Debra N. Welchel, Woodstock, GA (US); Ming Xie, Marietta, GA (US); Megan Christine Hansen Smith, Roswell, GA (US); Herb Flores Velazquez, Neenah, WI (US); Matrice Brown Jackson, Woodstock, GA (US); Andrew Joseph Beltz, Neenah, WI (US); Ralph Andrew Solarski, Alpharetta, GA (US); Russell J. Kroll, Woodstock, GA (US); Philip D. Palermo, Marietta, GA (US); Suzuko Hisata, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 240 days.

(21) Appl. No.: 11/413,576

(22) Filed: Apr. 28, 2006

(65) Prior Publication Data
US 2007/0252946 A1 Nov. 1, 2007

(51) Int. Cl.
G02C 1/00 (2006.01)
A61F 9/00 (2006.01)

(52) U.S. Cl. ............................ 351/158; 2/8.2

(58) Field of Classification Search .................. 351/41, 351/111, 121, 158; 2/8.2, 173
See application file for complete search history.

(56) References Cited

U.S. PATENT DOCUMENTS

| | | | |
|---|---|---|---|
| 1,026,272 A | 5/1912 | Leveque | |
| 1,562,350 A | 11/1925 | Luckey | |
| 3,377,626 A | 4/1968 | Smith | |
| 4,209,234 A | 6/1980 | McCooeye | |
| 4,250,577 A | 2/1981 | Smith | |
| 4,419,993 A | 12/1983 | Petersen | |
| 4,638,728 A | 1/1987 | Elenewski | |
| 4,796,621 A | 1/1989 | Barle et al. | |
| 4,799,782 A | 1/1989 | Tuttle | |
| 4,863,257 A | 9/1989 | Morgan | |
| 4,868,929 A | 9/1989 | Curcio | |
| 4,937,880 A | 7/1990 | Beard | |
| 4,942,626 A | 7/1990 | Stern et al. | |
| 4,944,039 A * | 7/1990 | Dietrich | 2/13 |
| 5,107,543 A | 4/1992 | Hansen | |

(Continued)

FOREIGN PATENT DOCUMENTS

DE 3323670 1/1985

(Continued)

OTHER PUBLICATIONS

Patent Abstracts of Japan, JP 2005215324, Publication Date: Aug. 11, 2005.

(Continued)

*Primary Examiner*—Huy K Mai
(74) *Attorney, Agent, or Firm*—Nathan P. Hendon; Sue C. Watson

(57) ABSTRACT

Eyewear having adapters and/or mask attachment features which permit the eyewear to attach to a mask, or a mask to attach to the eyewear. An adapter may be used which may provide a portion of the eyewear and/or mask. Alternatively, an adapter may be provided separately. Finally, a flap adapter may be used to extend facial protection for eyewear.

20 Claims, 3 Drawing Sheets

U.S. PATENT DOCUMENTS

| | | | |
|---|---|---|---|
| 5,162,823 | A | 11/1992 | Goldstein |
| 5,191,364 | A | 3/1993 | Kopfer |
| 5,319,397 | A | 6/1994 | Ryden |
| 5,351,339 | A | 10/1994 | Reuber et al. |
| 5,363,153 | A * | 11/1994 | Bailiff .......................... 351/78 |
| 5,363,512 | A | 11/1994 | Grabos, Jr. et al. |
| 5,416,536 | A | 5/1995 | Tee, Jr. |
| 5,419,318 | A | 5/1995 | Tayebi |
| 5,457,505 | A | 10/1995 | Canavan et al. |
| 5,459,533 | A | 10/1995 | McCooeye et al. |
| 5,517,700 | A | 5/1996 | Hoffman |
| 5,584,078 | A * | 12/1996 | Saboory .......................... 2/427 |
| 5,610,669 | A | 3/1997 | Kuipers et al. |
| 5,652,637 | A | 7/1997 | Marini |
| 5,720,281 | A | 2/1998 | Allen et al. |
| 5,898,468 | A | 4/1999 | Mage |
| 5,907,385 | A | 5/1999 | Flores et al. |
| 5,956,117 | A | 9/1999 | Suh et al. |
| 5,956,119 | A * | 9/1999 | Gibbs .......................... 351/158 |
| 5,969,787 | A | 10/1999 | Hall et al. |
| 6,094,751 | A | 8/2000 | Parks |
| 6,318,369 | B1 | 11/2001 | Gregory |
| 6,637,038 | B1 | 10/2003 | Hussey |
| 6,701,537 | B1 | 3/2004 | Stamp |
| 6,783,235 | B1 | 8/2004 | Lin |
| 6,959,988 | B1 | 11/2005 | Sheldon |
| 7,077,137 | B2 * | 7/2006 | Russell .................. 128/206.12 |
| 2003/0035082 | A1 | 2/2003 | Olney |
| 2004/0066486 | A1 | 4/2004 | Yi |
| 2004/0069302 | A1 | 4/2004 | Wilson et al. |
| 2004/0100384 | A1 | 5/2004 | Chen et al. |
| 2004/0107483 | A1 | 6/2004 | Thorson |
| 2004/0125334 | A1 | 7/2004 | Olney |
| 2005/0012893 | A1 | 1/2005 | Yamamoto |
| 2005/0160521 | A1 | 7/2005 | Hussey |
| 2005/0174470 | A1 | 8/2005 | Yamasaki |
| 2005/0237477 | A1 | 10/2005 | Lindahl |
| 2005/0270478 | A1 | 12/2005 | Curci et al. |
| 2005/0286734 | A1 | 12/2005 | Wang |
| 2006/0001827 | A1 | 1/2006 | Howell et al. |

FOREIGN PATENT DOCUMENTS

| | | |
|---|---|---|
| GB | 264280 | 1/1927 |
| GB | 489530 | 7/1938 |
| GB | 2362472 | 11/2001 |
| WO | WO 97/04837 | 2/1997 |
| WO | WO 97/50013 | 12/1997 |
| WO | WO 98/39682 | 9/1998 |
| WO | WO 99/55180 | 11/1999 |
| WO | WO 02/02039 | 1/2002 |
| WO | WO 2004/098715 | 11/2004 |

OTHER PUBLICATIONS

Patent Abstracts of Japan, JP 2005269572, Publication Date: Sep. 29, 2005.

* cited by examiner

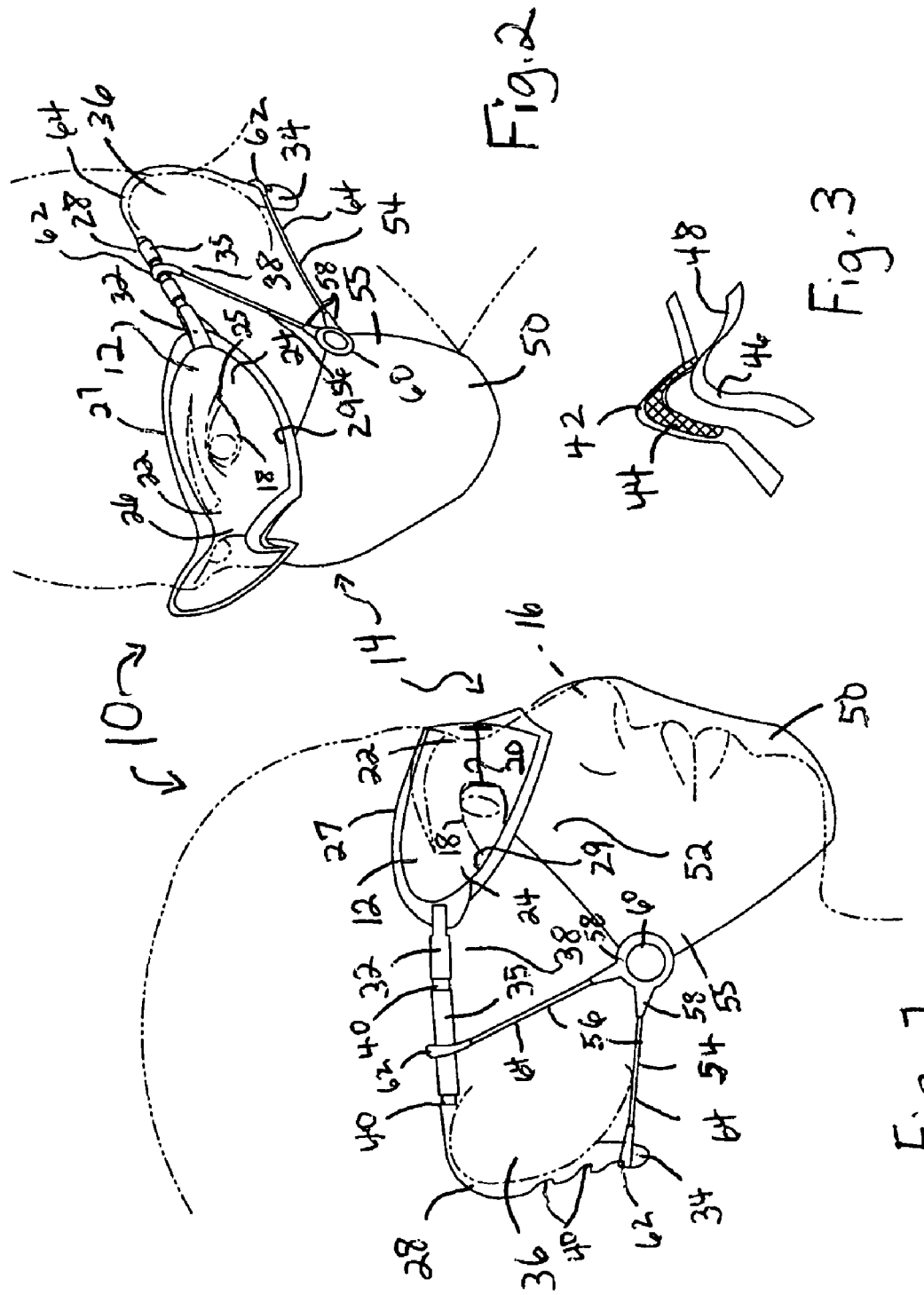

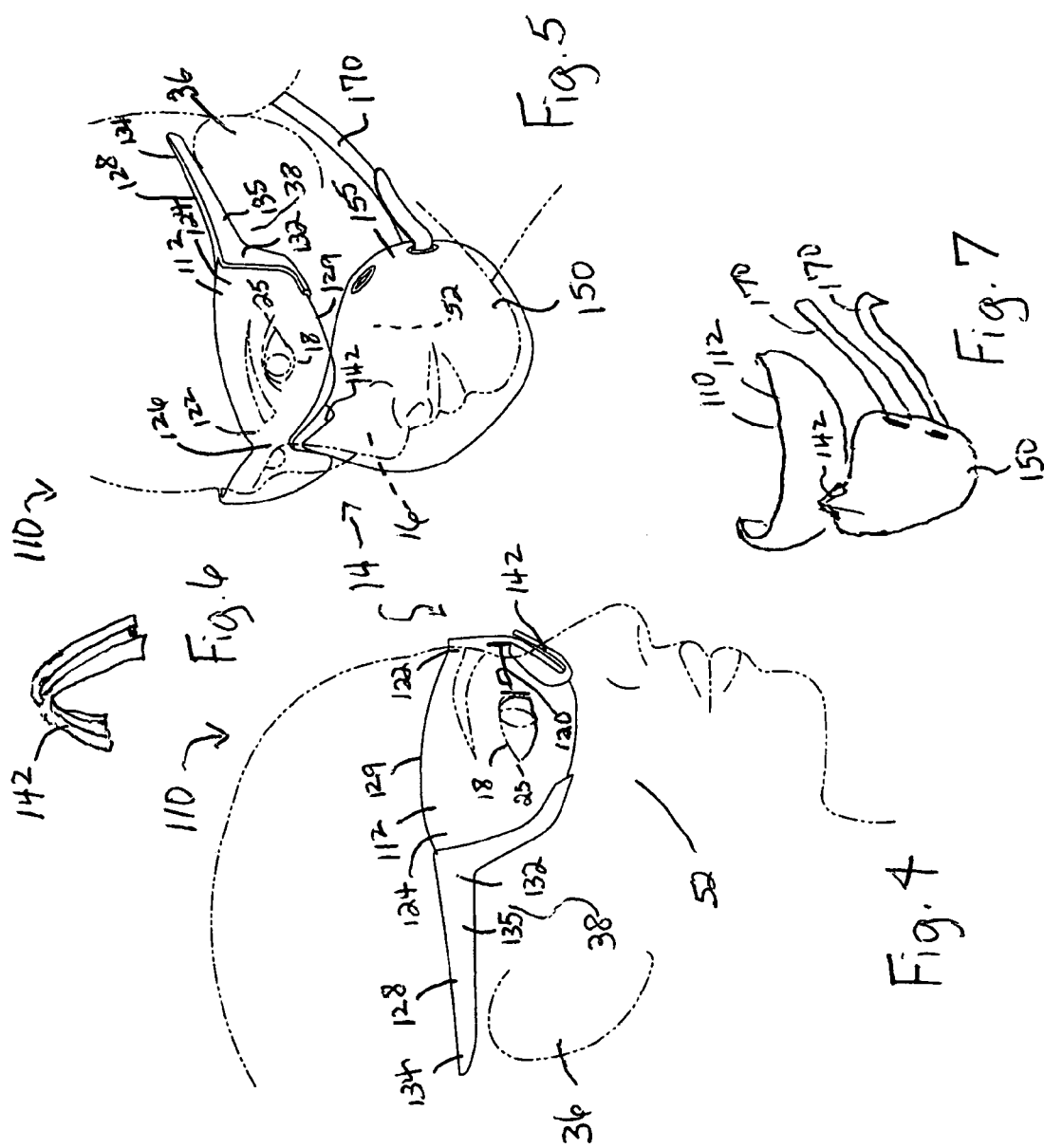

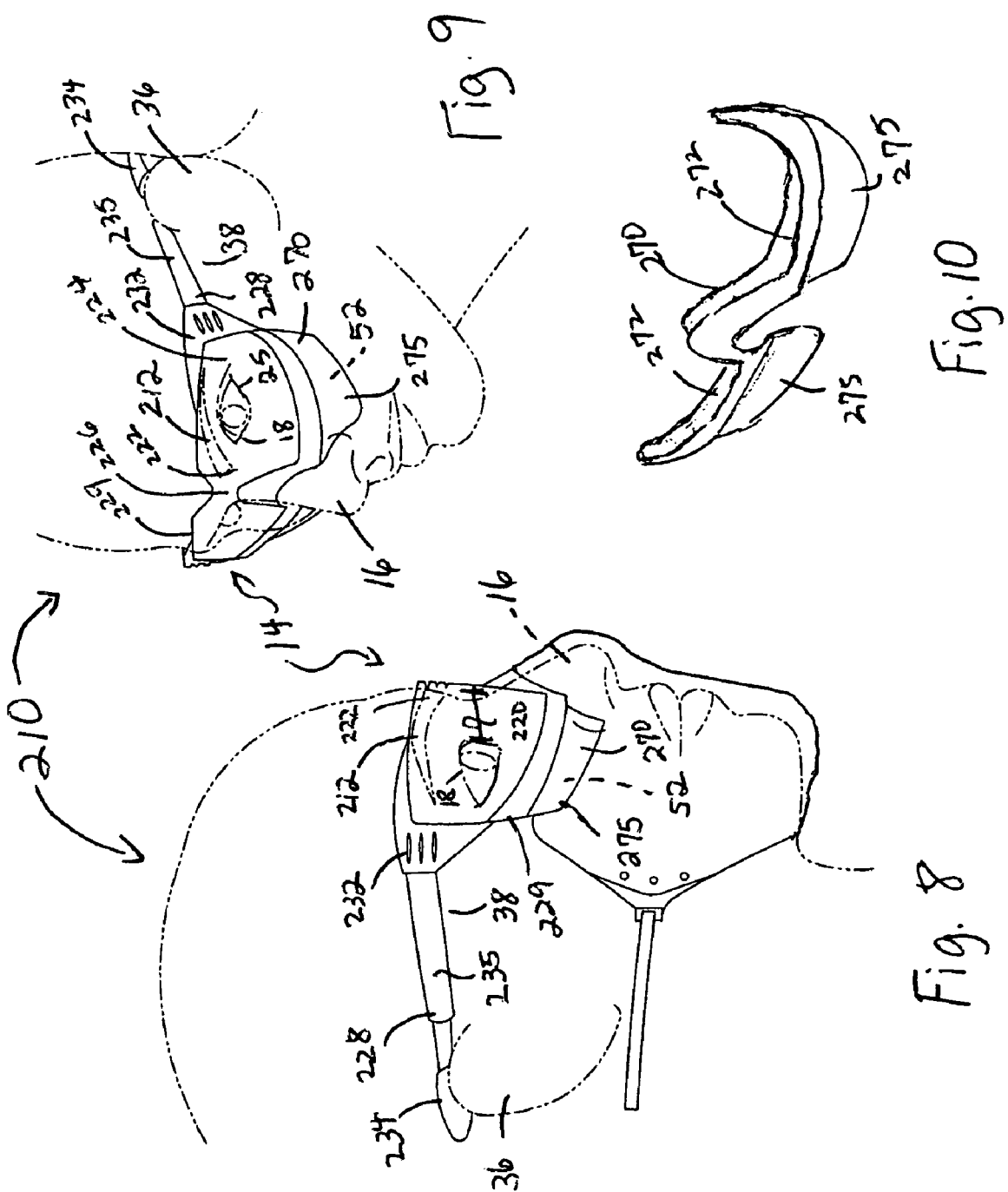

EYEWEAR WITH MASK ATTACHMENT FEATURES

BACKGROUND OF THE INVENTION

This invention relates to eyewear, and especially eyewear used for safety and/or activities such as sports.

Eyewear for safety applications in industrial use are used to protect a user's eyes. Such eyewear is usually designed to fit relatively closely to a user's face, so that noxious gas, liquid, particles, contaminants, and the like, do not touch or affect a user's eye(s). Similarly, masks are often required as well, to protect a user's face as well as to filter and remove such contaminants from the air.

Safety glasses or eyewear are often designed and formed such that they are bulky and heavy to wear. Some are tight-fitting and uncomfortable as well, such as goggles or masks. In addition, such eyewear is often provided as in only a few sizes which do not fit every user's face well. In addition, masks often need to overlap the eyewear, or, alternatively, the eyewear needs to overlap the mask. This results in a poor fit and possible introduction of contaminants into both the eyewear and the mask. Further, this combination is often uncomfortable and limits vision and/or breathing. This results in poor compliance in users donning and wearing the eyewear with a mask.

Therefore, safety eyewear which is lightweight, adjustable and provides a compatible fit against a mask, as well as a mask which provides a compatible fit against safety eyewear would be desirable. Such eyewear desirably provide comfortable and adequate protection for a user's eyes while having an adapter built into the eyewear. Alternatively, such an adapter may be provided separately. In addition, it would be desirable to have a mask which has features which permit it to easily couple to safety eyewear without either the eyewear or the mask having significant and uncomfortable overlap. Such eyewear and masks desirably would provide protection for a user's eyes while providing design features which makes the eyewear more attractive to wear.

Definitions

As used herein, the term "glasses" or "eyewear" refers to eyeglasses, goggles, or other objects worn over the eyes.

As used herein, the terms "ear piece" or "ear pieces" refers to The portion of glasses or eyewear which extends from a lens and/or frame to extend over and/or about a portion of a user's ear to assist in holding the glasses or eyewear on a user's head.

As used herein, the phrase "custom fit" refers to an item that is provided or made in a proper size, shape and fit for the individual, particularly, to fit the contours of a certain area of an individual's body (For example, "These shoes were made to fit my feet very well.").

As used herein, the term "contour" refers to at least a portion of an item which is shaped to fit the outline or form of something (Example, "A contour sheet").

As used herein, the term "hinge" or "hinges" refers to a jointed or flexible device that connects and permits pivoting or turning of a part to a stationary component. Hinges include, but are not limited to, metal pivotable connectors, such as those used to fasten a door to frame, and living hinges. Living hinges may be constructed from plastic and formed integrally between two members. A living hinge permits pivotable movement of one member in relation to another connected member.

As used herein, the terms "contaminate", "contaminant" and/or "contamination" mean to make unclean or impure by contact. Such contact may be by liquid, solid and/or gas. For example, but not by way of limitation, mud that befouls shoes; noxious fumes that foul the air; bodily fluids that foul clean diapers.

As used herein, the term "fasteners" means devices that fasten, join, connect, secure, hold, or clamp components together. Fasteners include, but are not limited to, screws, nuts and bolts, rivets, snap-fits, tacks, nails, loop fasteners, and interlocking male/female connectors, such as fishhook connectors, a fish hook connector includes a male portion with a protrusion on its circumference. Inserting the male portion into the female portion substantially permanently locks the two portions together.

As used herein, the term "couple" includes, but is not limited to, joining, connecting, fastening, linking, or associating two things integrally or interstitially together.

As used herein, the term "configure" or "configuration" means to design, arrange, set up, or shape with a view to specific applications or uses. For example: a military vehicle that was configured for rough terrain; configured the computer by setting the system's parameters.

As used herein, the term "substantially" refers to something which is done to a great extent or degree; a significant or great amount; for example, as used herein "substantially" as applied to "substantially" covered means that a thing is at least 90% covered.

As used herein, the term "alignment" refers to the spatial property possessed by an arrangement or position of things in a straight line or in parallel lines.

As used herein, the terms "orientation" or "position" used interchangeably herein refer to the spatial property of a place where or way in which something is situated; for example, "the position of the hands on the clock."

As used herein, the term "about" refers to an amount that is plus or minus 10 percent of a stated or implied range.

As used herein, the term "resilient" and "resiliency" refers to the physical property of an object and/or a material that can return to its original shape or position after deformation that does not exceed its elastic limit.

As used herein, the term "mask" refers to any type of mask or respirator known to be used or worn by human users.

These terms may be defined with additional language in the remaining portions of the specification.

SUMMARY OF THE INVENTION

The present invention is directed to eyewear for protecting a user's eyes. The eyewear includes at least one lens which extends a distance from the user's face and which is configured to cover the user's eyes from the distance. The lens has a first portion positioned adjacent the user's nose, a second portion positioned adjacent an outer edge of the user's eye, and an outer edge. The eyewear also include a pair of ear pieces attached to at least a portion of the eyewear and at least one adapter coupled to a portion of the eyewear, where the adapter is configured to couple to a mask.

The present invention is also directed to an adapter that is adapted to hold eyewear to a mask. the adapter includes a coupling means that couples at least a portion of the eyewear to at least a portion of the mask such that the eyewear and mask are releasably coupled together.

Additionally, the present invention is also directed to an adapter that is adapted to couple to eyewear. The adapter includes a coupling means that the adapter is configured to couple to at east a portion of the eyewear and to extend downward to cover at least a portion of the user's face such that the adapter covers a portion of the user's cheeks. The adapter assists in preventing contaminants from contaminating the user's eyes and includes a pair of flaps.

Finally, the invention is also directed to an assembly that includes eyewear for protecting a user's eyes and a protective flap. The eyewear includes at least one lens and a pair of ear pieces coupled to a portion of the eyewear. The lens extends a distance from the user's face and is configured to cover the user's eyes from the distance. Additionally, the lens includes a first portion positioned adjacent the user's nose, a second portion positioned adjacent an outer edge of the user's eye, and an outer edge. The protective flap is configured to extend from one outer edge to an opposite outer edge of the user's eyes and across a portion of the user's nose. The flap extends over a portion of the user's cheeks to assist in protecting the user's eyes.

BRIEF DESCRIPTION OF THE DRAWINGS

FIG. 1 is a side view of the present invention, showing eyewear having a common lens extending across a user's eyes and a hook assembly assisting in holding a mask to the eyewear;

FIG. 2 is a perspective view of the eyewear of FIG. 1;

FIG. 3 is a perspective view of a portion of an eyewear nose piece having an eyewear coupler therein and a portion of a mask nose piece having a mask coupler therein;

FIG. 4 is a side view of another embodiment of the present invention showing a nose piece adapter releasably coupled to eyewear;

FIG. 5 is a perspective view similar to FIG. 4 but showing a mask coupled to the nose piece adapter;

FIG. 6 is a perspective view of one nose piece adapter;

FIG. 7 is a perspective view of a mask using a nose piece adapter to couple a mask to eyewear having only a lens and without ear pieces;

FIG. 8 is a side view of another embodiment of the present invention, showing eyewear having a flap adapter coupled thereto and having a mask therewith;

FIG. 9 is a perspective view similar to FIG. 8, but showing eyewear and a flap adapter without a mask; and FIG. 10 is a perspective view of the flap adapter of FIGS. 8 and 9.

DETAILED DESCRIPTION

Reference will now be made in detail to one or more embodiments of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Safety glasses and/or glasses used in sports applications are usually made with shatter-resistant plastic lenses to protect the eye. Although safety lenses may be constructed from a variety of materials that vary in impact resistance, certain standards suggest that they maintain a minimum 1 millimeter thickness at the thinnest point, regardless of material. Safety glasses can vary in the level of protection that they provide based on their intended application. For example, those used in medicine may be expected to protect against blood splatter while safety glasses in a factory might have stronger lenses and a stronger frame and may include additional shields or safety features. The lenses of safety glasses may be shaped for correction or magnification. Some safety glasses may also be designed to fit over corrective glasses or sunglasses.

While face shields, goggles, and so forth are available as well, some studies have suggested that they will not always be used due to their bulkiness and weight. Therefore, lighter weight eyewear, while not providing as much protection as full face shields and/or goggles, may be preferred and actually worn more frequently by users due to their lack of size or bulk and their reduced weight. In addition, recent studies have also suggested that when safety glasses are both light weight and have a more stylish design, these features in combination also result in a higher usage of safety glasses in the appropriate situations.

The lenses of safety glasses are desirably made from plastic. There are a number of suitable plastics which may be utilized. Examples of some plastics used for eyewear include polycarbonates, such as LEXAN® manufactured by General Electric, Fairfield, Conn., allyl diglycol polycarbonate such as CR-39® manufactured by PPG Industries, Pittsburgh, Pa., and thermoplastic elastomers (TPE) such as Kraton® or Dynaflex® produced by GLS, McHenry, Ill.

Other materials may also be available for making lenses; other materials may be added to or provided via, for example, but not by way of limitation, a coating, cover, and so forth provided to the lenses to provide additional features. Such features may include, but are not limited to ultraviolet (UV) light protection, anti-fogging protection, anti-reflective (AR) protection, and so forth. Safety and/or sports glasses may desirably be ranked according to meeting certain requirements. In the United States, the American National Standards Institute (ANSI) has various standards and ratings for safety glasses. Safety glasses may be rated according to their ability to resist, for example, flying debris, heat, sparks, acid splash, abrasive blasting materials, glare, radiation, and so forth.

Safety and/or sports glasses may have numerous uses in a household situation. Safety glasses may be used while painting, while cutting grass, and so forth. Many different types of sports have found protective eyewear useful as well. Safety glasses or eyewear are increasingly needed for new industrial, home and sports applications.

The eyewear desirably enhances a user's performance when worn in combination with disposable masks and/or respirators. The eyewear and the mask desirably cooperates to work with a user's facial geometry such that each is easy to put on, wear and remove, and each fits a user's face and performs its function without interfering with the other.

Referring now to FIGS. 1-10 in general, and FIGS. 1 and 2 in particular, the present invention provides eyewear adapted to protect a user's eyes. In the present embodiment, the eyewear 10 includes at least one lens 12. The lens may include a single lens 12 which extends generally across a user's face 14 and specifically across a user's nose 16 to cover both eyes 18 and thereby to provide protection to both eyes 18. Alternatively, the eyewear may include a pair of lenses (not shown).

Desirably the lens 12 extends a distance 20 from the user's eyes and is configured to cover or extend over each of a user' eyes 18 from the distance 20 to provide protection thereto, as illustrated in FIGS. 1 and 2. The lens 12 desirably includes at least one, and in this embodiment a pair of first portions 22 which are positioned adjacent a user's nose 16. The lens 12 desirably also includes a pair of second portions 24 which are positioned adjacent an outer edge 25 of a user's eye 18. The lens 12 includes a connector 26 which is positioned across a user's nose 16. The lens 12 may include a frame 27 positioned about at least a portion of an outer edge 29 of the lens 12, although the lens 12 may be provided without a frame (not shown).

A pair of ear pieces 28 are desirably coupled to the lens and/or the frame. In the present embodiment, the ear pieces 28 are coupled to a portion of the frame 27. Each ear piece 28 is configured to hold the lens 12 adjacent a user's face 14. Desirably, each ear piece 28 includes a first end 32 and a second end 34. A temple piece 35 desirably extends between the first end 32 and the second end 34.

The first end 32 of each ear piece 28 is desirably pivotably coupled near the second portions 24 of the lens 12. The second end 34 desirably is positioned over and/or around a portion of a user's ear 36 when the eyewear 10 is being worn. Similarly, the temple piece 35 is desirably configured to be positioned adjacent a user's temple 38.

The temple piece 35 and a portion of the second end 34 may include a plurality of notches 40 therein. Each notch 40 may include a magnet, adhesive, such as, but not by limitation, a cohesive adhesive, frictional elements such as, for example, rubber bumps or ribs, or other connecting mechanisms known in the art. Alternatively, any portion of the ear pieces 28 may include one or more apertures.

The frame 27 (or lens) desirably includes a nose piece 42 which is positioned over a user's nose 16. The nose piece 42 desirably includes an adapter or eyewear coupler 44 which permits it to couple to an associated adapter or mask coupler 46 provided on a nosepiece 48 of a mask 50.

The eyewear coupler 44 may be positioned on another location of the eyewear 10, so long as it cooperates with an associated mask coupler 46 on the mask 50, which would also be located in another position. Usually, however, it is contemplated that a desirable location for coupling eyewear 10 and the mask together would be adjacent a user's nose 14 and/or cheeks 52, but such locations are intended as non-limiting. The eyewear coupler 44 and the mask coupler 46 may provide a cooperative mechanical couple, such as a tongue on the eyewear coupler and a groove and the mask coupler. Alternatively, the the eyewear coupler and/or the mask coupler may use an adhesive, such as a pressure sensitive adhesive. In yet another alternative, the eyewear coupler and the mask coupler may use a cohesive adhesive. In still yet another embodiment, the eyewear coupler and the mask coupler may include a hook and loop material. It will be appreciated that other mechanical fasteners may also be used as the eyewear coupler and the mask coupler.

In the present embodiment, however, the eyewear coupler 44 and the mask coupler 46 include magnets. That is, the eyewear coupler 44 and the mask coupler 46 each include magnets which attract each other. Therefore, the eyewear 10 and the mask 50 are held in a releasably coupled arrangement due to the magnetic attraction between the eyewear coupler 44 and the mask coupler 46.

The mask 50 may be attached to the eyewear via a hook assembly. The hook assembly 56 desirably permits a peripheral portion 55 of the mask 50 to be coupled to a user's face 14. The hook assembly 54 includes a plurality of hook connectors 56, each of which includes, at a coupled end 58 which is coupled to a fastener 60 which desirably releasably coupled to the peripheral portion 55 of the mask 50. Each hook connector 56 desirably includes, at an opposite end, a hook 62. Each hook 62 may include a coupling mechanism, such as rubber, magnets, and so forth. A cord 64 desirably extends between each end 58 and each hook 62.

In the present embodiment, each hook 62 includes a magnet which is attracted to the one or more magnets position in the each of the plurality of notches 40 such that the magnetic attraction assists in coupling the mask 50 to the eyewear 10. Alternatively, however, if the ear pieces 28 include one or a plurality of apertures, each hook may be positioned in an aperture to assist in holding the mask to the eyewear (not shown).

It will be appreciated that the eyewear 10 may be donned and worn by a user without the mask 50. Similarly, it will be appreciated that the mask 50 may be worn without the eyewear 10 and without the hook assembly. In addition, the mask 50 may be coupled to the eyewear 10 via a connection only between the mask coupler 46 and the eyewear coupler 44 (not shown). In another alternative, the eyewear 10 may be coupled to the mask 50 only by use of the hook assembly 54 (not shown).

In another embodiment of the invention, the eyewear 110 and mask 150 shown in FIGS. 4-7 is similar to the eyewear 10 shown in FIGS. 1-3 and described in detail previously herein, except that the eyewear 110 and mask 150 has some features which differ from those of eyewear 10 and mask 50.

Referring now to FIGS. 4-7, the present invention provides eyewear adapted to protect a user's eyes. In the present embodiment, the eyewear 110 includes at least one lens 112. The lens may include a single lens 112 which extends generally across a user's face 14 and specifically across a user's nose 16 to cover both eyes 18 and thereby to provide protection to both eyes 18. Alternatively, the eyewear may include a pair of lenses (not shown).

Desirably the lens 112 extends a distance 120 from the user's eyes 18 and is configured to cover or extend over each of a user's eyes 18 from the distance 120 to provide protection thereto. The lens 112 desirably includes at least one, and in this embodiment a pair of first portions 122 which are positioned adjacent a user's nose 16. The lens 112 desirably also includes a pair of second portions 124 which are positioned adjacent an outer edge 25 of a user's eye 18. The lens 112 includes a connector 126 which is positioned across a user's nose 16. The lens 112 may include a frame (not shown) positioned about at least a portion of an outer edge 129 of the lens 112, although the lens 112 may be provided without a frame, as shown.

A pair of ear pieces 128 are desirably coupled to the lens and/or the frame. In the present embodiment, the ear pieces 128 are each coupled to the lens adjacent second portions 124 thereof. Each ear piece 128 is configured to hold the lens 112 adjacent a user's face 14. Desirably, each ear piece 128 includes a first end 132 and a second end 134. A temple piece 135 desirably extends between the first end 132 and the second end 134.

The first end 132 of each ear piece 128 is desirably pivotably coupled on or near to the lens 112. The second end 134 desirably is positioned over and/or around a portion of a user's ear 36 when the eyewear 110 is being worn. Similarly, the temple piece 135 is desirably configured to be positioned adjacent a user's temple 38.

The lens 112 (or frame, when provided) desirably includes a releasable nose piece adapter 142 which is configured to be positioned over a user's nose 16, as shown in FIG. 6. The nose piece adapter 142 may desirably includes two sides. One side may includes an eyewear adapter 144 which permits the nose piece adapter 142 to couple to the eyewear 110. The opposite side of the nose piece adapter 142 may include a mask adapter 146, which permits the nose piece adapter 142 to couple to a nose piece 148 of a mask 150, to hold the eyewear 110 and the mask 150 together. While the adapter 142 is provided as a nose piece, it will be understood that other adapters may be used in other or adjacent locations to releasably couple the eyewear 110 to the mask 150 (not shown). Accordingly, a nose piece is intended as a non-limiting embodiment.

The nose piece adapter 142 may provide a cooperative mechanical coupling, such as a tongue on the eyewear and a groove on the adapter 142, or vice versa, which cooperatively couple together; the same is true for the coupling of the nose piece adapter 142 with the mask 150. Accordingly, the nose piece adapter 142 may use any coupling means shown and/or described herein, or known in the art. The adapter 142 may also be provided as a separate component of a standard removable nose piece, or the adapter 142 may be provided separately to couple to such a nose piece or the eyewear 110.

In the present embodiment, however, the nose piece adapter 142 provides a nose piece as well as an adapter for coupling to a mask 150, as illustrated in FIGS. 4 and 5. This coupling may permit one or more straps 170 which may couple to a peripheral portion 155 of the mask 150 to be removed so that a user has less bulk and the mask 150 is still well secured to a user's face via the adapter 142 which holds the nose piece 148 of the mask 150 to the eyewear 110.

In another alternative, the mask 150 may be coupled to a user's face 14 and the nose piece adapter 142 may be coupled between the mask 150 and eyewear 110. In this instance, however, as illustrated in FIG. 7, the eyewear 110 does not include ear pieces, and may only include a single lens 112 which coupled to the mask 150 via the nose piece adapter 142. In this instance, it is the eyewear 110 which is unencumbered with ear pieces because the adapter 142 and mask 150 cooperate to hold the eyewear 110, that is, the single lens of FIG. 7 in a position over a user's eyes 18.

In another embodiment of the invention, the eyewear 210 and mask 250 shown in FIGS. 8-10 are very similar to the eyewear 110 shown in FIGS. 4-7 and described in detail previously herein, except that the eyewear 210 and mask 250 may be used and interconnected with a flap adapter 270 instead of with an adapter.

Referring now to FIGS. 8-10, the present invention provides eyewear adapted to protect a user's eyes. In the present embodiment, the eyewear 210 includes at least one lens 212. The lens may include a single lens 212 which extends generally across a user's face 14 and specifically across a user's nose 16 to cover both eyes 18 and thereby to provide protection to both eyes 18. Alternatively, the eyewear may include a pair of lenses (not shown).

Desirably the lens 212 extends a distance 220 from the user's eyes 18 and is configured to cover or extend over each of a user eyes 18 from the distance 220 to provide protection thereto. The lens 212 desirably includes at least one, and in this embodiment a pair of first portions 222 which are positioned adjacent a user's nose 16. The lens 212 desirably also includes a pair of second portions 224 which are positioned adjacent an outer edge 25 of a user's eye 18. The lens 212 includes a connector 226 which is positioned across a user's nose 16. The lens 212 may include a frame (not shown) positioned about at least a portion of an outer edge 229 of the lens 212, although the lens 112 may be provided without a frame, as shown.

A pair of ear pieces 228 are desirably coupled to the lens and/or the frame. In the present embodiment, the ear pieces 228 are each coupled to the lens 212 adjacent second portions 224 thereof. Each ear piece 228 is configured to hold the lens 212 adjacent a user's face 14. Desirably, each ear piece 228 includes a first end 232 and a second end 234. A temple piece 235 desirably extends between the first end 232 and the second end 234.

The first end 232 of each ear piece 228 is desirably pivotably coupled near to the lens 212. The second end 234 desirably is positioned over and/or around a portion of a user's ear 36 when the eyewear 210 is being worn. Similarly, the temple piece 235 is desirably configured to be positioned adjacent a user's temple 38.

A flap adapter 270, as illustrated in FIG. 10, is provided and may be worn with the eyewear 212. The flap adapter 270 desirably, but not by way of limitation, provides a groove 272 which follows the contours of the outer edge 229 of the lens 212 and connector 226 and a lower portion 274 thereof. The flap adapter 270 has a pair of flaps 275 which extend downward to rest against a user's cheeks 52. The flaps 275 operate to provide additional protection to the eyewear 212 against the admission of contaminants which might otherwise obtain entry under the eyewear 212, as illustrated in FIG. 9. The flap adapter 270 also permits a mask 250 to be worn with the eyewear 212 and flap adapter 270.

In this instance, the flap adapter 270 may provide comfort and cushioning so that the mask 250 does not interfere with the eyewear 212, but can be worn comfortably over a portion of the flap adapter 270, as shown in FIG. 8. In addition, the flap adapter 270 may include an adapter as described previously herein, which permits the mask 250 to be coupled to a portion of the flap adapter 270 (not shown).

The flap adapter 270 is desirably formed from a soft material and resilient, flexible material, such as, for example, but not by way of limitation, silicone, urethane, and so forth. The flap adapter 270 may be disposable or reusable, and it may include features which permit moisture to be wicked away from a user's face, such as, by way of non-limiting example, superabsorbents, desiccants, and so forth. The flap adapter 270 may be coupled to the eyewear 210 and/or the mask 250 by any means shown and/or described herein.

It will be appreciated that the features and/or components of one embodiment may be combined, in whole or in part, with another embodiment. In some circumstances, such combination may yield yet another embodiment.

While the present invention has been described in connection with certain preferred embodiments, it is to be understood that the subject matter encompassed by way of the present invention is not to be limited to those specific embodiments. On the contrary, it will be appreciated that some elements and/or articles may be used with other elements or articles. It is intended for the subject matter of the invention to include all alternatives, modifactions and equivalents as can be included within the spirit and scope of the invention.

What is claimed is:

1. Eyewear adapted for protecting a user's eyes, including;
   at least one lens which extends a distance from a user's face and which is configured to cover a user's eyes from the distance, the lens having a first portion positioned adjacent a user's nose and a second portion positioned adjacent an outer edge of a user's eye, the lens including an outer edge;
   a pair of ear pieces attached to at least a portion of the eyewear, wherein each ear piece includes at least one magnet;
   at least one adapter coupled to a portion of the eyewear, the adapter configured to couple to a mask; and
   a hook assembly including a fastener and a hook connector which couples between a mask and the ear piece, the hook connector having at least one magnet which is configured to magnetically couple to the ear piece and the fastener configured to couple to a peripheral portion of a mask such that the hook assembly holds a mask to the eyewear when it is coupled thereto.

2. The eyewear of claim 1, wherein the adapter includes connecting means which permits it to couple to both eyewear and the mask.

3. An adapter adapted to couple to eyewear, the adapter including coupling means such that the adapter is configured to couple to at least a portion of the eyewear and to extend downward to cover at least a portion of a user's face such that the adapter covers a portion of a user's cheeks and assists in preventing contaminants from contaminating a user's eyes, wherein the adapter includes a pair of flaps.

4. The adapter of claim 3, wherein the coupling means includes a magnet provided in the adapter, and wherein the eyewear further comprises a magnet which operates to permit the eyewear to releasably couple to the adapter.

5. The adapter of claim 3, wherein the coupling means includes a hook and loop material provided in the adapter, and wherein the eyewear further comprises a hook and loop material which operates to permit the eyewear to releasably couple to the adapter.

6. The adapter of claim 3, wherein the coupling means includes an adhesive provided on the adapter, and wherein the eyewear further comprises an adhesive which operates to permit the eyewear to releasably couple to the adapter.

7. The adapter of claim 3, wherein the coupling means includes at least one of a tongue and groove member provided in the adapter, and wherein the eyewear further comprises one of a tongue and groove member which operates to permit the eyewear to releasably couple to the adapter.

8. The adapter of claim 3, wherein the adapter is coupled to a mask and to eyewear, and wherein the eyewear does not include ear pieces and the mask and adapter cooperate to hold the eyewear in a position over a user's eyes.

9. The adapter of claim 3, further comprising a mask coupled with the adapter.

10. An assembly, comprising:
    eyewear for protecting a user's eyes, including;
        at least one lens which extends a distance from a user's face and which is configured to cover a user's eyes from the distance, the lens having a first portion positioned adjacent a user's nose and a second portion positioned adjacent an outer edge of a user's eye, the lens including an outer edge,
        a pair of ear pieces coupled to a portion of the eyewear; and
    a protective flap, the flap configured to be positioned adjacent to a lower edge of the lens, the flap configured to extend from one outer edge to an opposite outer edge of a user's eyes and across a portion of a user's nose, the flap extending downward from the lower edge of the lens and over a portion of a user's cheeks to assist in protecting a user's eyes.

11. The assembly of claim 10, wherein the flap is formed from a resilient material.

12. The assembly of claim 11, wherein the flap includes silicone.

13. The assembly of claim 11, wherein the flap includes urethane.

14. The assembly of claim 10, wherein the flap has an upper edge which includes a groove which is configured to receive a lower edge of the lens.

15. The assembly of claim 11, wherein the assembly further includes a mask.

16. Eyewear adapted for protecting a user's eyes, including;
    at least one lens which extends a distance from a user's face and which is configured to cover a user's eyes from the distance, the lens having a first portion positioned adjacent a user's nose and a second portion positioned adjacent an outer edge of a user's eye, the lens including an outer edge;
    a pair of ear pieces attached to at least a portion of the eyewear;
    at least one adapter coupled to a portion of the eyewear, the adapter configured to couple to a portion of a mask; and
    a hook assembly which is adapted to releaseably couple a different portion of the mask and the ear piece, where the hook assembly comprises a fastener and a hook connector, where the hook connector is configured to releaseably couple to the ear piece and the fastener is configured to releaseably couple to a peripheral portion of the mask such that the hook assembly holds the mask to the eyewear when it is coupled thereto.

17. The eyewear of claim 16, where the at least one adapter is coupled to a portion of the eyewear adjacent the first portion.

18. The eyewear of claim 16, where the hook assembly further comprises a cord extending between the hook connector and the fastener.

19. The eyewear of claim 16, where the hook assembly comprises a pair of hook assemblies which are configured to releaseably couple a mask to each of the ear pieces.

20. The eyewear of claim 16, further comprising a mask coupled to the eyewear.

* * * * *